United States Patent [19]

Stanfill

[11] 4,036,591
[45] July 19, 1977

[54] METHOD FOR PLACING A CORROSION TEST SPECIMEN INTO AN ENVIRONMENT TO BE TESTED

[75] Inventor: Herman F. Stanfill, Brea, Calif.

[73] Assignee: Union Oil Company of California, Brea, Calif.

[21] Appl. No.: 715,241

[22] Filed: Aug. 18, 1976

[51] Int. Cl.² ............... G01N 31/00; G01N 33/20
[52] U.S. Cl. ............... 23/230 C; 21/2.5 R; 73/86; 427/156
[58] Field of Search ............ 21/2.5 R; 23/230 C; 73/86; 427/156; 204/1 T, 195 C

[56] References Cited
U.S. PATENT DOCUMENTS

| | | | |
|---|---|---|---|
| 2,492,848 | 12/1949 | Crouch et al. | 427/156 |
| 3,080,747 | 3/1963 | Kerst | 73/86 X |
| 3,711,249 | 1/1973 | Keeney | 23/230 C X |
| 3,840,439 | 10/1974 | Marsh | 204/195 C X |

Primary Examiner—Morris O. Wolk
Assistant Examiner—Michael S. Marcus
Attorney, Agent, or Firm—Richard C. Hartman; Dean Sandford

[57] ABSTRACT

A method for protecting the prepared surface of a corrosion test specimen from a contaminating environment while the specimen is being placed in an environment to be tested. After the surface has been prepared, the specimen is encapsulated in ice which protects it from exposure to the contaminating environment. The ice melts after the ice-encapsulated specimen has been placed into the environment to be tested, thereby exposing the prepared surface.

6 Claims, No Drawings

METHOD FOR PLACING A CORROSION TEST SPECIMEN INTO AN ENVIRONMENT TO BE TESTED

BACKGROUND OF THE INVENTION

1. Field of the Invention

This invention relatees to corrosion measurement, and more particularly to methods for placing a corrosion specimen into an environment to be tested.

2. Description of the Prior Art

It has long been the practice in the monitoring of the corrosion rates of matals exposed to a corosive environment to place corrosion test specimens, such as probes or coupons, in the corrosive environment. The corrosion rate of the metal in the particular environment is determined by the change in weight of these specimens as a function of the exposure time. Additionally, visual inspection of the specimens can reveal the type of corrosion which has occurred, such a a uniform general corrosion or a more localized attack such as pitting.

The measured corrosion rate and the determined type of corrosion are subsequently used as the base for selection of a corrosion protection system. Similarly, the specimen can be used to monitor the effectiveness of corrosion protection systems. Often, specimens of proposed construction materials for a structure are exposed to the expected environment in order to determine their susceptibility to corrosion.

In many cases, the environment of interest is not directly accessible and the specimen must be passed through one or more contaminating environments. Exposure to a corrosive or erosive gas can accelerate the subsequent corrosion rate. Also, exposure to a liquid hydrocarbon or other film-forming compositions can leave a corrosion-inhibiting film. In these cases, the measured corrosion rate may not be representative of the actual corrosion rate and may not represent the corrosion type.

In particular, the measurement of corrosion in the bottom of oil storage tanks, in which a liquid hydrocarbon layer floats on an underlying aqueous corrosive layer, presents a problem. A corrosion test specimen which is to be placed in the aqueous layer must be passed through the upper hydrocarbon layer. The specimen will usually acquire a hydrocarbon film which will inhibit corrosion until the film has been dissipated. The dissipation time is dependent on the hydrocarbon type and the texture and uniformity of the surface of the corrosion specimen. In the case where the hydrocarbon film is uneven or borken, corrosion of the specimen would vary across the surface and give the appearance of localized attack even if there would be little localized attack without the hydrocarbon film. Since the choice of a corrosion protection system depends on the type as well as the rate of corrosion, examination of an improperly exposed specimen could result in the selection of an improper or inadequate system. The results of such selection could be unchecked corrosion or, conversely, expensive over-protection. In a few instances, such as when chemical corrosion inhibitors are used to provide an anodic coating, an improper choice of inhibitor concentration or type can actually convert a minor, general corrosion problem into a servere localized corrosion problem.

Thus, need exists for a method for protecting the prepared surface of a corrosion specimen from a contaminating environment while the specimen is being placed in the environment to be tested.

Accordingly, a principal object of this invention is to provide a method for monitoring corrosion.

Yet another object of this invention is to provide an improved method for placement of corrosion test specimens into an environment to be tested.

Still another object of this invention is to provide a method for protecting the prepared surface of corrosion test specimens from contamination by a hostile environment during their placement into the environment of interest.

A further object of this invention is to provide a method for protecting the prepared surface of a corrosion test specimen from acquiring a hydrocarbon film while the specimen is passed through the hydrocarbon layer of an oil storage tank and into the aqueous layer to be tested.

Other objects and advantages of this invention will become apparent to those skilled in the art from the following description.

SUMMARY OF THE INVENTION

Briefly, this invention provides a method for protecting the prepared surface of a corrosion test specimen from a contaminating environment while the specimen is being placed into an environent to be tested. After its surface has been prepared, the specimen is immersed in water. The water is subsequently frozen, thereby forming an ice capsule around the specimen. The ice capsuel is kept frozen until the specimen has been placed into the environment to be tested. Thereafter, the ice is allowed to melt, thereby exposing the prepared surface to the environment to be tested. The method of this invention is particularly suited for passing a specimen through the contaminating hydrocarbon layer in an oil storage tank and into the bottom aqueous layer which is to be tested.

DETAILED DESCRIPTION OF THE INVENTION

It is common practice in the petroleum industry to install corrosion test specimens, such as metal coupons or probes, in an environment to evaluate its corrosiveness and to monitor the effectiveness of corrosion prevention measures. These specimens are also used to evaluate the suitability of different metals in the corrosive environment.

There are many types of specimens. Some of the more common ones are strip, round and washer-type circular coupons. Coupons are normally made of a mild steel. It is desirable, however, to use metal alloys similar to the alloys used in the structure or alloys that are being considered for the structure. The method of this invention is also applicable to the placement of electrochemical type corrosion testing robes such as disclosed in U.S. Pat. Nos. 3,398,065 and 3,840,489 to G. A. Marsh, or electrical resistance type corrosion testing probes such as those disclosed in U.S. Pat. Nos. 3,197,724, 3,207,983 and 3,222,920 to E. Schaschl and G. A. Marsh.

A specimen is normally prepared by (1) cutting it from a metal sheet; (2) machine etching or metal punching a permanent serial number on it for identification, and (3) subsequently preparing its surface by one of several techniques. The National Associaton of Corrosion Engineers' technical practices committee published a recommended practice pamphlet, NACE Standard RP-07-75, entitled "Preparation and Installation of Corrosion Coupons and Interperetation of Test Data in Oil Production Practice". This Standard discloses the minimum standards and the minimum acceptable surface preparation and installation techniques recommended by the NACE under normal circumstances. More detailed methods of surface preparation are given by M. Henthorne, "Measuring Corrosion in the Process Plant", Chemical Engineering, August 25, 1971, pp. 89–94, and F. A. Champion, Corrosion Testing Procedures, John Wiley & sons, 1962. The disclosures of these references are herein incorporated by reference.

The various surface preparaton techniques are used to prepare a representative surface. In the gross measurement of corrosion rates in an oil storage tank or pipeline, the specimen surface might include a scratch and/or a weld in order to simulate the surface inperfections where the corrosion rate might be accelerated, whereas in the more exacting measurement of intrinsic corrosion susceptibility of various metal alloys, a very carefully prepared uniform surface is necessary. In almost all cases, the surface must be cleaned of hydrcarbon films and hydrocarbon or metal grit. corrosion rates are often accelerated at edges and cold-worked surfaces. Accordingly, edges are usually coated with epoxy and excessive cold working of the specimen is either avoided, or its effects are removed by annealing. These surface preparation techniques are well known in the art.

After surface preparation, the specimens are normally handled with clean gloves to avoid contaminating the surface with oils, grit or moisture. Traditionally, prepared specimens are stored and shipped in moisture-proof envelopes containing water inhibitors such as silica gel and/or contaminating-vapor inhibitors such as activated charcoal. However, these precautionary measures cannot prevent contamination of the surface if the specimen must be passed through a contaminating environment during its placement.

Contaminating environments include erosive high velocity gas or liquid streams; corrosive gases such as steam and hydrogen sulfide-containing gases; corrosive compositions such as acids, sea water and aerated aqueous solutions; corrosion-inhibiting compositons such as aqueous solutins of corrosion inhibitors; and film-forming compositons such as hydrocarbons, polymers, latices, gels, etc.

The ice may be formed from any aqueous solution which does not itself corrode the specimen or cause the subsequent corrosion of the specimen to be accelerated or inhibited. Although distilled and/or deionized water is preferred, other aqueous solutions could be used subject to the foregoing restrictions.

In a preferred embodiment of this invention, a corrosion test specimen is prepared from a sheet of mild steel or other metal according to the techniques recommended in the NACE Standard RP-07-75. One or more insulated wires or non-electrically conductive cords, by which the secimen may be supported or suspended in the environment to be tested, are attached to the specimen and thereafter the points of attachment and the specimen edges are coated with epoxy to prohibit corrosion at these surfaces. Alternately, the specimen can be supported by electrically insulated rigid supports. The prepared specimen is then completely immersed in distilled water suspended by its supporting wires. The water and specimen are then cooled until the water freezes, thereby forming an ice coating preferably at least one eighth-inch thick and more preferably at least one half-inch thick on each surface of the specimen, completely encapsulating the specimen. In any case, the thickness of the ice capusle must be sufficient to ensure that the surface is not exposed prior to its placement in the environment to be tested. The encapsulated specimen is then positioned in that environment according to techniques recommended in the NACE Standard RP-07-75. Once positioned, the ice will melt to expose the clean, prepared surface. The size and shape of the corrosion test specimen and ice capsule will depend on the individual structure involved and the corrosive environment.

This invention is further illustrated by the following examples which are illustrative of specific modes of practicing the invention and are not intended as limiting the scope of the invention as defined by the appended claims.

EXAMPLE 1

To monitor the corrosion rate in an operating pipeline, a corrosion probe is inserted through a valve and packing gland assembly. The 2-inch by ½-inch diameter cylindrical probe is immersed in water in a 2½-inch cylindrical container of ⅜-inch internal diameter. The water is frozen thereby forming a 2-⅜-inch by 178-inch diameter ice capsule. The ⅜-inch ice capsule is then inserted through the ⅜-inch opening in the packing gland assembly and into the interior of the pipeline. After placement, the ice melts to expose the uncontaminated probe. After 30 days the probe is removed and the changes in its weight and physical appearance are observed in order to determine the rate and type of corrosion.

EXAMPLE 2

In order to monitor the effectiveness of a water-soluble corrosion inhibitor which has been added to the bottom aqueous layer of liquid contained in a mild-steel storage tank, a corrosion specimen of mild steel is lowered into the aqueous layer. The ⊖ by 3 by 6-inch metal coupon is prepared according to the surface preparation techniques set forth in the NACE Standaard RP-07-75. The ends and edges of the coupon are covered with an epoxy resin to prohibit corrosion at these points and the coupon is suspended, fully immersed, in distilled water. The water is frozen in order to give a 1 by 7-inch ice capsual. The encapsulated specimen is maintained refrigerated and transported to the tank site, then lowered through the hydrocabon layer and into the underlying aqueous layer. The ice melts to expose the prepared surface to the aqueous layer containing the corrosion inhibitor. After 60 days the coupon is removed and cleaned with solvent according to standard practices. The change in weight and appearance of the corrosion coupon are observed in order to evaluate the rate and type of corrosion which are occurring with the corrosion inhibitor as compared to that which occurred to the coupons tested prior to adding the corrosion inhibitor.

While particular embodiments of the invention have been described, it will be understood, of course, that the invention is not limited thereto since many obvious modifications can be made, and it is intended to include within this invention any such modifications as will fall within the scope of the claims.

Having now described the invention, I claim:

1. A method for passing a corrosion test specimen through a contaminating environment and into an environment to be tested, which comprises:

encapsulating said specimen in ice; and passing said specimen through said contaminating environment and into said test environment.

2. The method defined in claim 1 wherein said contaminating environment is a corrosive or erosive gas or liuqid stream.

3. The method defined in claim 1 wherein said contaminating environment contains a corrosion inhibiting composition.

4. The method defined in claim 3 wherein said corrosion inhibiting composition.

5. The method defined in claim 4 wherein said contaminating environment is oil and said environment to be tested is an underlying aqueous layer.

6. In a method for measuring the corrosion rate in the aqueous layer of a hydrocarbon storage tank which comprises (1) passing a corrosion test specimen through hydrocarbon layer of said tank and into said aqueous layer; (2) removing said coupon from said layers of said tank after a period of exposure; and (3) measuring the change in weight and/or appearance of said specimen, the improvement which comprises:

encapsulating said specimen in ice;

passing the ice-encapsulated specimen through said hydrocarbon layer and into said aquoues layer; and allowing the ice to melt.

* * * * *